United States Patent
Giselbrecht et al.

(10) Patent No.: US 7,402,708 B2
(45) Date of Patent: Jul. 22, 2008

(54) METHOD FOR PRODUCING AQUEOUS ORTHO-PHTHALALDEHYDE SOLUTIONS

(75) Inventors: Karlheinz Giselbrecht, Pasching (AT); Wolfgang Hillisch, Leonding (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 0 days.

(21) Appl. No.: 11/338,727

(22) Filed: Jan. 25, 2006

(65) Prior Publication Data

US 2006/0199870 A1    Sep. 7, 2006

(30) Foreign Application Priority Data

Mar. 2, 2005    (AT) ............................... A 354/2005

(51) Int. Cl.
*C07C 45/00*    (2006.01)

(52) U.S. Cl. ...................................... 568/430; 568/438
(58) Field of Classification Search ........................ None
See application file for complete search history.

(56) References Cited

U.S. PATENT DOCUMENTS 5,872,153 A * 2/1999 Giselbrecht et al. ......... 514/699
6,486,358 B1 * 11/2002 Giselbrecht et al. ......... 568/438

* cited by examiner

*Primary Examiner*—Sikarl A Witherspoon
(74) *Attorney, Agent, or Firm*—Nixon & Vanderhye P.C.

(57) ABSTRACT

A method for producing aqueous ortho-phthalaldehyde solutions which comprises introducing an acetal of the o-phthalaldehyde into water and subsequently setting a pH <7 by adding an acid, whereupon, then at a temperature between 10° C. and 90° C., the acetal is converted into the o-phthalaldehyde by eliminating the corresponding alcohol, and also use of OPA acetals for producing these solutions.

12 Claims, No Drawings

METHOD FOR PRODUCING AQUEOUS ORTHO-PHTHALALDEHYDE SOLUTIONS

The invention relates to a method for producing aqueous ortho-phthalaldehyde solutions from ortho-phthalaldehyde acetals.

Aqueous solutions of ortho-phthalaldehyde (OPA) are used in the biocide sector. In particular, these solutions are used in the sector of high-activity disinfection of endoscopes, and also for the disinfection of medical equipment.

Hitherto, aqueous solutions of OPA have been produced by dissolving an appropriate amount of OPA in water. OPA is a solid and occurs in crystalline form and, in this form has some disadvantages, since it is toxic and leads to skin irritations, so that handling OPA is made difficult and considerable safety precautions are required in formulating aqueous OPA solutions. In addition, OPA has a tendency to cake, as a result of which, firstly problems occur in charging, and secondly lengthy dissolution processes are required.

OPA itself is produced, as described, for example in EP 0 839 789, by saponifying liquid OPA acetals which act as storage compounds for OPA. The saponification is performed in accordance with the above literature by hydrolysis at a pH between 0 and 7 using mineral acids, such as HCl, $H_2SO_4$, $H_3PO_4$, or organic acids, such as acetic acid, formic acid, p-toluenesulfonic acid or methanesulfonic acid.

The use of OPA or OPA acetals for producing aqueous OPA-glutaraldehyde solutions which are likewise used in the biocide sector is disclosed, for example, by EP 0 843 966, according to which an aqueous OPA-glutaraldehyde solution is obtained by cleavage of an OPA acetal in aqueous glutaraldehyde solution and removing the alcohol which is eliminated.

It was an object of the present invention to produce aqueous OPA solutions with the disadvantages of the use of crystalline OPA being avoided.

The present invention therefore relates to the production of aqueous ortho-phthalaldehyde solutions which comprises introducing an acetal of the o-phthalaldehyde into water and subsequently setting a pH <7 by adding an acid, whereupon, then at a temperature between 10° C. and 90° C., the acetal is converted into the o-phthalaldehyde by eliminating the corresponding alcohol.

In the inventive method, an OPA acetal is introduced or emulsified into water and dissolved by hydrolysis. As OPA acetal, dialkylacetals (open-chain acetals) or dialkoxyphthalanes (cyclic acetals of OPA) having 1 to 6 carbon atoms in the alkyl moiety come into consideration. Preference is given to dialkoxyphthalanes or dialkylacetals having 1 to 4 carbon atoms in the alkyl moiety, particularly preferably having 1 to 2 carbon atoms in the alkyl moiety.

According to the invention, sufficient acetal is introduced into water and dissolved, so that after acidifying, a 0.025 to 9% strength by weight aqueous OPA solution is obtained. Preference is given to 0.05 to 5% strength by weight solutions, particularly preferably 0.5 to 2% strength by weight solutions.

It must be noted here that the equilibrium in the aqueous solution, according to $^1$H-NMR, lies at 25% OPA, and 75% OPA hemiacetals.

In order to obtain more highly concentrated solutions, it is possible to add to the solution a solubilizer, for example polyethylene glycol, or water-miscible solvents from the group of ketones, for instance N-methylpyrrolidone, acetone, etc., the aldehydes, for instance glutaraldehyde, etc., as a result of which OPA-concentrations up to 50% by weight can be obtained.

To convert the acetal to OPA, an acid is added to the aqueous solution so that a pH of less than 7 is set. As acid, mineral acids, for instance sulfuric acid, HCl etc., or organic acids, for instance formic acid, acetic acid, glyoxylic acid, etc. come into consideration. Preferably, sulfuric acid, glyoxylic acid or formic acid is used.

The pH should be below 7, preferably up to 5, particularly preferably up to 3.

The cleavage is performed at a temperature of 10 to 90° C., preferably at 20 to 50° C. Preferably, the solution is stirred.

If the acetal is placed in water, there is first a 2-phase emulsion which only converts into a homogeneous solution after the pH is set to below 7.

It is advantageous in the inventive method that, compared with the use of OPA itself, more highly concentrated solutions (9% compared with 5%) can be produced, since the alcohol eliminated by the acidification favors the dissolution of the OPA formed.

If appropriate, after the cleavage, the resultant aqueous OPA solution can be neutralized, or set to a pH of 4 to 10, preferably up to 8, for example by adding inorganic bases such as $NaHCO_3$, NaOH, KOH, etc.

In addition, if desired, the alcohol being eliminated can be removed from the solution by distilling it off, as a result of which, however, the solubility is reduced again to 5%.

Furthermore, in addition to the abovementioned solubilizers, other customary aids, for instance stabilizers, antioxidants, fragrances, dyes, etc. can be added to the solution produced according to the invention.

The aqueous OPA solutions produced according to the invention are particularly suitable for use in the biocide sector and are distinguished, in particular, by the fact that, first, the final production step for OPA is omitted due to the direct use of the acetal, which saves costs and, secondly, significant handling advantages are given by the use of the OPA acetal.

The inventive production of the aqueous OPA solutions, however, can also be performed in automated disinfection apparatuses.

The invention further relates to the use of OPA acetals as starting material for the production of aqueous OPA solutions which are used in the biocide sector.

EXAMPLE 1

OPA solutions of different concentrations were produced from OPA dimethylacetal-water-acid mixtures.

The reaction conditions (acid used, pH, temperature, % by weight) and the time until a clear homogeneous solution was obtained (complete cleavage) are apparent from the tables hereinafter.

TABLE 1 pH: 1.0 using sulfuric acid

| A | B | Time at 25° C. to clear solution (min): | Time at 35° C. to clear solution (min): | Time at 45° C. to clear solution (min): |
|---|---|---|---|---|
| 0.7 | 0.5 | 15 | 7.5 | 3.75 |
| 1.3 | 1 | 15 | 7.5 | 3.75 |
| 2.7 | 2 | 30 | 15 | 7.5 |
| 4.0 | 3 | 40 | 20 | 10 |
| 5.4 | 4 | 45 | 22.5 | 11.25 |
| 6.7 | 5 | 60 | 30 | 15 |
| 8.1 | 6 | 80 | 40 | 20 |
| 9.4 | 7 | 90 | 45 | 22.5 |
| 10.7 | 8 | 150 | 75 | 37.5 |
| 13.4 | 9 | 330 | 165 | 82.5 |

A: OPA-acetal concentration used in % by weight
B: OPA concentration in solution in % by weight

TABLE 2 pH: 2.0 using sulfuric acid

| A | B | Time at 25° C. to clear solution (min): |
|---|---|---|
| 1.3 | 1 | 15 |
| 4.0 | 3 | 120 |
| 9.4 | 7 | 400 |

TABLE 3 pH: 2.0 using glyoxylic acid:

| A | B | Time at 25° C. to clear solution (min): |
|---|---|---|
| 0.7 | 0.5 | 30 |
| 1.3 | 1 | 60 |
| 2.7 | 2 | 90 |
| 4.0 | 3 | 120 |
| 6.7 | 5 | 480 |

TABLE 4 pH: 2.0 using acetic acid

| A | B | Time at 25° C. to clear solution (min): |
|---|---|---|
| 0.7 | 0.5 | 15 |
| 1.3 | 1 | 20 |
| 2.7 | 2 | 60 |
| 4.0 | 3 | 120 |
| 5.4 | 4 | 240 |

TABLE 5 pH: 2.0 using formic acid

| A | B | Time at 25° C. to clear solution (min): |
|---|---|---|
| 1.3 | 1 | 20 |
| 2.7 | 2 | 90 |
| 4.0 | 3 | 150 |
| 5.4 | 4 | 300 |

The invention claimed is:

1. A method for producing an aqueous ortho-phthalaldehyde solution which comprises the steps of:

(a) forming a precursor solution by introducing an acetal of the o-phthalaldehyde into water, (b) acidifying the precursor solution to a pH <7 by adding an acid to the precursor solution, (c) forming an aqueous ortho-phthalaldehyde solution consisting of ortho-phthalaldehyde, water and the eliminated corresponding alcohol by bringing the acidified precursor solution obtained according to step (b) to a temperature between 10° C. and 90° C. to thereby convert the acetal into o-phthalaldehyde by eliminating the corresponding alcohol, and (d) retaining the corresponding alcohol eliminated according to step (c) in the aqueous ortho-phthalaldehyde solution so as to aid in the dissolution of the converted o-phthalaldehyde therein.

2. The method as claimed in claim 1, wherein the acetal of the o-phthalaldehyde is a dialkylacetal or a dialkoxyphthalane having 1 to 6 carbon atoms in the alkyl moiety.

3. The method as claimed in claim 1, wherein step (b) is practiced by adding to the precursor solution a mineral acid or an organic acid.

4. The method as claimed in claim 1, wherein the precursor solution is acidified to a pH up to 3.

5. The method as claimed in claim 1, wherein the aqueous o-phthalaldehyde solution obtained by steps (a) through (d) contains between 0.025 to 9% by weight o-phthalaldehyde.

6. The method as claimed in claim 1, further comprising adding to the precursor solution a solubilizer which is at least one selected from the group consisting of polyethylene glycol, N-methylpyrrolidone, acetone and glutaraldehyde.

7. The method as claimed in claim 1, further comprising adding to the precursor solution at least one aid selected from the group consisting of stabilizers, antioxidants, fragrances and dyes.

8. The method as claimed in claim 1, further comprising after step (c) the step of neutralizing the aqueous o-phthalaldehyde solution to a pH of 4 to 10 by adding a base thereto.

9. The method as claimed in claim 1, wherein the aqueous ortho-phthalaldehyde solution is produced in an automated disinfection apparatus.

10. The method as claimed in claim 3, wherein the mineral acid is at least one selected from the group consisting of sulfuric acid and hydrochloric acid.

11. The method as claimed in claim 3, wherein the organic acid is at least one selected from the group consisting of formic acid, acetic acid and glyoxylic acid.

12. An aqueous ortho-phthalaldehyde solution which consists of o-phthalaldehyde, water and a corresponding alcohol eliminated by an acidified reaction of an acetal of the o-phthalaldehyde.

* * * * *